United States Patent [19]
Bernard

[11] Patent Number: 5,873,849
[45] Date of Patent: Feb. 23, 1999

[54] ELECTRODES AND ELECTRODE ARRAYS FOR GENERATING ELECTROPORATION INDUCING ELECTRICAL FIELDS

[75] Inventor: Robert M. Bernard, Rancho Santa Fe, Calif.

[73] Assignee: Ichor Medical Systems, Inc., San Diego, Calif.

[21] Appl. No.: 845,553

[22] Filed: Apr. 24, 1997

[51] Int. Cl.$^6$ ........................................... A61N 1/30
[52] U.S. Cl. ............................ 604/20; 607/116; 607/148
[58] Field of Search ...................... 607/115, 116, 607/148, 152, 153; 128/642, 907; 604/20, 21

[56] References Cited

U.S. PATENT DOCUMENTS

| | | |
|---|---|---|
| 3,957,053 | 5/1976 | Woo ........................................ 607/116 |
| 3,991,755 | 11/1976 | Vernon . |
| 4,141,359 | 2/1979 | Jacobsen . |
| 4,250,878 | 2/1981 | Jacobsen . |
| 4,381,789 | 5/1983 | Naser et al. ........................ 607/148 X |
| 4,398,545 | 8/1983 | Wilson . |
| 4,837,049 | 6/1989 | Byers et al. ........................ 607/115 X |
| 5,019,034 | 5/1991 | Weaver . |
| 5,058,605 | 10/1991 | Slovak ................................ 607/148 X |
| 5,128,257 | 7/1992 | Baer . |
| 5,215,088 | 6/1993 | Normann et al. .................... 607/116 X |
| 5,273,525 | 12/1993 | Hofmann . |
| 5,298,017 | 3/1994 | Theeuwes . |
| 5,304,120 | 4/1994 | Crandell . |
| 5,389,069 | 2/1995 | Weaver . |
| 5,439,440 | 8/1995 | Hofmann . |
| 5,462,520 | 10/1995 | Hofmann . |
| 5,464,386 | 11/1995 | Hofmann . |
| 5,468,223 | 11/1995 | Mir . |
| 5,501,662 | 3/1996 | Hofmann . |
| 5,507,724 | 4/1996 | Hofmann . |
| 5,545,130 | 8/1996 | Hofmann . |
| 5,547,467 | 8/1996 | Pliquett . |
| 5,667,491 | 9/1997 | Pliquett . |
| 5,674,267 | 10/1997 | Mir . |
| 5,676,646 | 10/1997 | Hofmann . |
| 5,688,233 | 11/1997 | Hofmann . |
| 5,695,459 | 12/1997 | Meguro ..................................... 604/20 |
| 5,702,359 | 12/1997 | Hofmann . |
| 5,704,908 | 1/1998 | Hofmann . |
| 5,749,847 | 5/1998 | Zewert . |

*Primary Examiner*—Jeffrey R. Jastrzab
*Attorney, Agent, or Firm*—James C. Weseman, Esq.; The Law Offices of James C. Weseman

[57] ABSTRACT

Electrodes and electrode array apparatus and systems for in vivo delivery of electrical waveforms rendering therapeutic benefit to the patient by utilizing an electrode array having at least three individually addressable electrodes disposed so as to form a triangle in a plane intersecting the electrodes and an electrical signal generating device operatively connected to the electrodes for delivering electrical waveforms to said electrodes and generating electroporation-inducing electrical fields between the electrodes.

21 Claims, 14 Drawing Sheets

| TRICELL ELECTRODE STATES | | | |
|---|---|---|---|
| | A | B | C |
| COMB. 1 | + | − | − |
| COMB. 2 | − | + | − |
| COMB. 3 | − | − | + |

TRI-GRID ELECTRODE STATES

| | A | B | C | D |
|---|---|---|---|---|
| COMB. 1 | + | + | − | − |
| COMB. 2 | + | − | + | − |
| COMB. 3 | + | − | − | + | though the needle arrays are described as adjustable in depth, there is no
ELECTRODES AND ELECTRODE ARRAYS FOR GENERATING ELECTROPORATION INDUCING ELECTRICAL FIELDS

TECHNICAL FIELD

The present invention relates to the delivery of electrical waveforms and, more particularly, to the design of electrodes and electrode arrays for efficiently delivering electrical waveforms in vivo.

BACKGROUND OF THE INVENTION

There exists a broad range of potential applications for the in vivo delivery of electrical waveforms, including bone repair, dermal wound healing, nerve regeneration, transport and delivery of therapeutic agents, and the like. Certain known techniques utilizing such electrical waveforms are generally referred to as iontophoresis, electro-osmosis, electroporation, and electropermeabilization. As there is limited understanding of the phenomenon known as electroporation, the terms electroporation and electropermeabilization are often used interchangeably.

Iontophoresis involves the application of electric currents to drive or repel oppositely charged particles through tissue. Iontophoretic devices have been known since the early 1900's. U.S. Pat. Nos. 3,991,755; 4,141,359; 4,398,545 and 4,250,878 disclose examples and some applications of such devices.

Electro-osmosis occurs when an electric field is applied parallel to a charged surface in contact with a solution. The net ion movement causes a hydrodynamic flow of all molecules which are nearby in the solution (Dimitrov et al. (1990)). During electroporation, the transport of therapeutic agent across the cell membrane is commonly believed to involve diffusion, the movement of molecules from areas of higher concentration to areas of lower concentration. This transmembrane movement into the cytosol of electroporated cells may be enhanced by electro-osmosis (Sowers (1992) pp. 120–125).

Electroporation refers to the application of electric fields of sufficient intensity and duration as to induce transient increases in cell membrane permeability. The cell membrane is a selectively permeable barrier that greatly inhibits the penetration of many therapeutic agents into the cytosol. As a comparative example, Mir et al. (1992) report a 10,000-fold increase in the cytotoxic activity of bleomycin, a normally impermeable chemotherapeutic agent, in the electroporated cells.

Rols et al. (1990) describe electroporation as a threshold dependent phenomenon in that electric field intensity must be higher than a critical threshold to induce cell permeability. They further report that the extent and duration of membrane permeabilization is dependent on pulse duration and number. Provided that the electric field strength was not too high and the pulse duration not too long, electroporation of the cell membrane appears reversible (Zimmerman (1986) pg 177). Thus there exists an opportunity for the use of electroporation of cell membranes to achieve therapeutic benefits. In order to achieve success, the electric fields propagated in tissue by the delivery of specific electrical waveforms must apply sufficient transmembrane voltage and pulse duration to induce cell membrane permeability, yet not exceed inherent upper limits leading to cell lysis (death).

Other than transdermal or transcutaneous applications, the in vivo electroporation of cell membranes is a relatively limited field. In U.S. Pat. No. 5,273,525 to Hofmann, and U.S. Pat. No. 5,389,069 to Weaver, a description is given of a two electrode system for acute placement during tissue electroporation.

Nishi, et al. (1996), Ceberg, et al. (1994), Salford, et al. (1993) and Okino, et al. (1987) also describe two electrode systems for tissue electroporation. Where described therein, the electrodes are of rod type (needle) construction, acutely placed in tissue, and spaced approximately 0.5–2 cm apart. However, the prior art does not provide clear guidance as to the need for uniformity in the electric field propagation. Additionally, there are not known to be methods for the confinement of threshold level field intensities to the targeted tissue.

As depicted in FIG. 1, panel A, the electric field propagated in tissue by a two electrode system 20a–20b as described in the prior art would be considerably weaker in the region of tissue that is proximal to the midpoint between the electrodes (represented as the dashed box 22). In fact, the field strength in the tissue will weaken geometrically as the distance from either electrode 20a, 20b is increased (panel B), and the field strength in the mid-region of tissue will also weaken geometrically as the distance "L" between the two electrodes is increased. As electroporation is considered to be a threshold-dependent phenomenon, with inherent upper limits due to the risk of cell lysis, a two electrode system is poorly suited to establish uniform electric field coverage, i.e., uniform electroporation, in the tissue targeted for treatment.

Plate-type electrodes 24a, 24b aligned in parallel (see FIG. 2) have been proposed to provide a uniform electric field 26 for electrochemotherapy delivered transcutaneously (U.S. Pat. No. 5,468,223 to Mir), and U.S. Pat. No. 5,439,440 to Hofmann describes an electrode for in vivo electroporation as spaced apart parallel arrays of needle electrodes 28a, 28b, 28c, 28d mounted on a dielectric support member 30 (see FIG. 3). This design allows adjustments in needle depth and spacing between the parallel arrays (separated by distance L), but not the spacing of electrodes within each array 32. As disclosed, the array design has features that suggest similarity to the plate-type electrodes of FIG. 2. However, in order to approach electric field uniformity (field 26 in FIG. 2), the spacing 32 between adjacent electrodes 28a, 28b in the same array would need to be in the range of 0.25 L or less. The anatomy of the tissue involved may limit the number of electrodes that can be spaced within the targeted region. If the spacing between adjacent electrodes on the array is much greater than 0.25 L, then the same field uniformity problems noted previously will remain for this array design. Furthermore, although the needle arrays are described as adjustable in depth, there is no disclosure providing a means to confine the field effects for deep tissue applications in the third dimensional axis relative to the electrode arrays.

Thus, it would be desirable to provide a means to propagate electric fields of adequate intensity for a three dimensional region of tissue so as to achieve uniform electroporation, while mitigating electric field-induced cell lysis. In addition, there is a need to confine such therapeutic field effect to the targeted region of tissue.

It is also considered desirable to provide the means to implement effective in vivo therapies utilizing electroporation that rely on: (i) adequate transmembrane voltages, i.e., adequate electric field intensities, propagated throughout a predetermined region of tissue, (ii) minimization of cell lysis due to electrical waveform delivery, most likely to occur in the electrode milieu where electric field intensities are the greatest, (iii) confinement of therapeutic electric field effects to the predetermined region of tissue, and (iv) adequate concentration of therapeutic agents in the extracellular space of the cells in the tissue being treated.

DISCLOSURE OF THE INVENTION

The present invention provides electrode and electrode array apparatus which facilitates the efficient delivery of electrical waveforms, and particularly delivery to a predetermined three dimensional region of tissue within a patient. Electrical waveforms of certain parameters, comprising many different therapeutic objectives and techniques, may be efficiently delivered through the present invention, while minimizing the risk of trauma to the patient.

In one aspect, the invention provides an electrode array having at least three individually addressable electrodes disposed so as to form a triangle in a plane intersecting the electrodes.

In another aspect of the invention, a system is provided wherein the electrode array is located in situ in a patient. When combined with elongate electrodes having defined conductive regions, the system defines a predetermined treatment region within the tissue of the patient.

A further aspect of the invention provides an elongate electrode apparatus having a means for connecting the electrode to a source of electrical signals, an electrically conductive region located distal to the connecting means, and an electrically nonconductive region located proximal to the connecting means.

The invention also provides an efficient means of expanding the electrode array "cell," or any alternative cell design, into a multi-cell grid for controlled electric field propagation in an expanded cross sectional area of the predetermined region. Penetrating the tissue, and designed for electric field confinement along one axis of the predetermined region, individual electrodes may be of varying lengths and proportions, comprising a distal electrically-conductive portion and a proximal electrically-nonconductive portion.

In certain embodiments, one can separately control each individual electrode, in order to achieve the desired therapeutic effect while minimizing attendant tissue trauma.

BRIEF DESCRIPTION OF THE DRAWINGS

FIGS. 12-1, 12-2, 12-3 depict the individual trilobe field patterns resulting from the four channel control means used to activate the tricells in a trigrid, with the arrows indicating the polarity along coincident lines;

DETAILED DESCRIPTION OF THE INVENTION

Figure 1A:
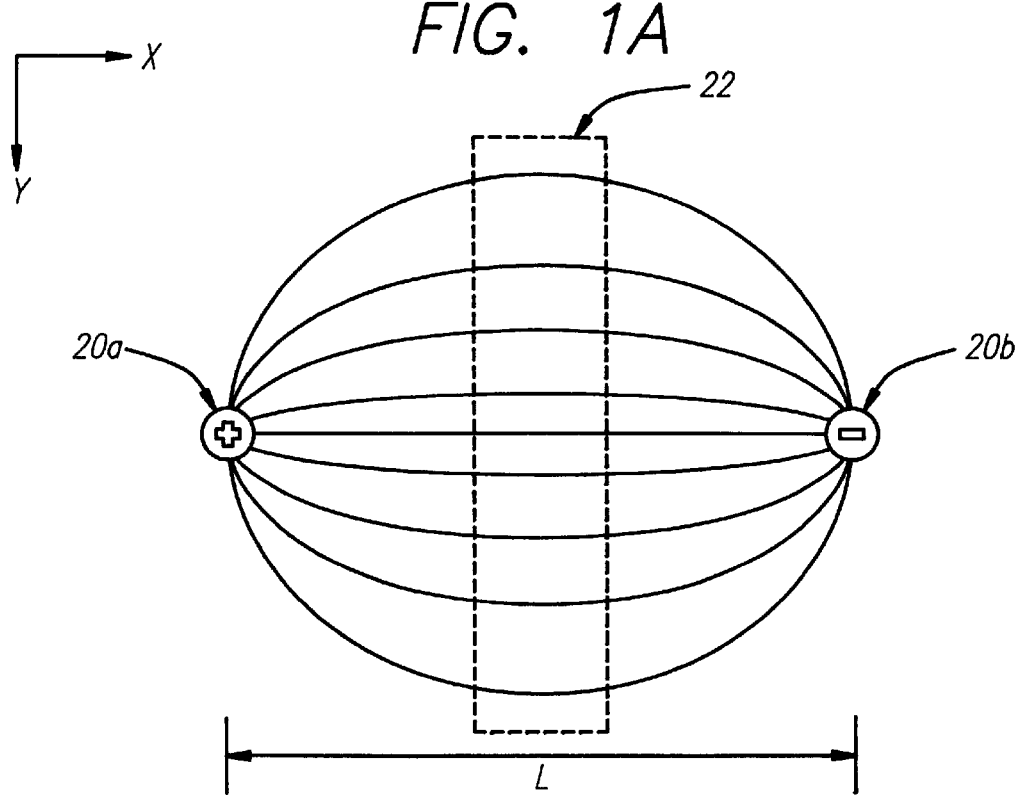
FIG. 1, panel A is a two dimensional schematic view depicting the field lines and approximate electric field intensity for a two electrode model, wherein the intraelectrode distance is L and the dashed box positioned midway between the two electrodes indicates the region of lowest electric field strength, and panel B is a graphic representation of the relationship between the distance from the electrode and the electric field strength.

The present invention provides apparatus and systems which facilitate the efficient delivery of electrical waveforms, and particularly such waveform delivery to a predetermined three dimensional region of tissue within a patient. Electrical waveforms of certain parameters, comprising many different therapeutic objectives and techniques, may be efficiently delivered through the present invention, while minimizing the risk of surgical trauma to the patient.

In one aspect, the invention provides an electrode array having at least three individually addressable electrodes disposed so as to form a triangle in a plane intersecting the electrodes. The electrodes can be provided in any form capable of conducting an electrical signal and establishing an electric field between oppositely-charged electrodes. Desirably, such electrodes will be of surgical quality, biocompatible, and capable of withstanding the demands of implantation and use in a patient. Materials commonly employed in the construction of such electrodes include nickel titanium, gold, silver, stainless steel, platinum, platinum iridium alloys, graphite, ceramic, and the like.

In certain embodiments, and in one aspect of the invention, the electrodes will be elongate, for example rod electrodes 34a, 34b, 34c (see FIG. 4), so as to simplify the surgical implantation of the electrode in the patient. Representative of such rod electrodes are needles such as acupuncture needles, which are usually of surgical quality, strength and (presumptively) bio-compatible stainless steel construction. However, it has been found that the relatively sharp point of such a needle electrode may provoke arcing of the electric field, particularly at the electrode delivering the electrons in the propagation of the electric field (i.e. the "pulse electrode"). Thus it has been found desirable to provide a rod electrode where the point of the electrode distal from the source of electrical signals includes a radius of curvature sufficient to substantially eliminate arcing at the electric field strengths utilized in the practice of the present invention, for example in the range of 0.1 to 1 mm. It has also been found that the diameter of the rod electrode has a similar effect on arcing potential, due in part to the relationship of the electrode diameter to the radius of curvature of the point. Therefore, the rod electrode itself will desirably also be of sufficient diameter to satisfy the arcing-reduction conditions as well.

Such elongate electrodes will desirably include a means for connecting to a source of electrical signals 36 and a non-conductive region 38 located proximal to the signal source. In this context the term "non-conductive" is taken to mean that the electrode does not permit an electric field to propagate radially from the electrode in the non-conductive region, while allowing the electrical signal or waveform to proceed axially or longitudinally through the non-conductive region. Such electrodes will also include a conductive region 40 located distal from the signal source. Optionally, there can be a plurality of conductive and non-conductive regions established in the electrode 34, for example where the distal-most region of the electrode is provided as a non-conductive region 41, in order to more precisely define the conductive region 40. Conveniently, these electrode regions 38, 40 (and optionally region 41) can be provided by shielding portions of the electrode 34 with a dielectric material, for example, with plastic, Teflon®, ceramic, graphite, polyimide, and the like. Alternatively, the electrode may be of composite construction, for example where the cross sectional diameter of the electrode is maintained relatively constant in order to facilitate insertion of the electrode 34 into the tissue of the patient.

Figure 4:
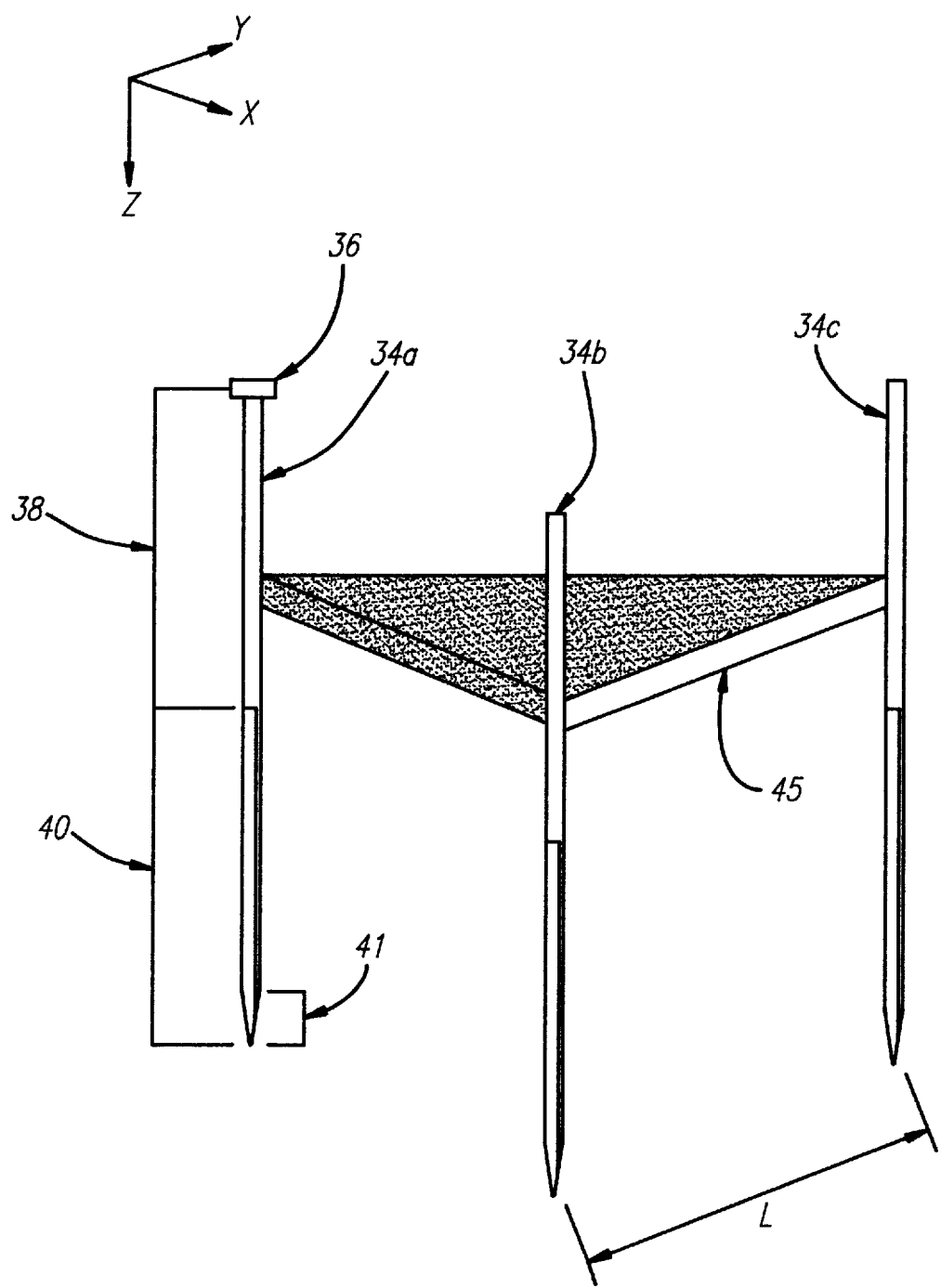
FIG. 4 depicts an electrode array configuration in accordance with the invention, exemplified as a tricell array mounted on a dielectric support member.

In addition to facilitating surgical implantation, such an electrode 34 with a nonconductive region 38 (and optionally region 41) will permit the establishment of a predetermined region of tissue for treatment, where two of the dimensions are established by the geometry of the electrode array, and the third dimension is established by the length of the conductive region 40 of the electrode 34, i.e. the "effective electrode length."For example, as also depicted in FIG. 4, one aspect of the invention is a three electrode array (termed a "tricell") comprising three elongate electrodes of predetermined length, disposed approximately parallel to each other, and spatially oriented in the "X" and "Y" dimensions of a three dimensional predetermined region, desirably in the approximate geometrical shape of an equilateral triangle. The "Z" or third dimension of the predetermined region is dependent on the effective electrode length established by the conductive region(s).

Thus, in another aspect of the invention, a system is provided wherein the present electrode array is located in situ in a patient. When combined with elongate electrodes having defined conductive regions establishing effective electrode lengths, the system defines a predetermined treatment region within the tissue of the patient. This predetermined treatment region can then be subject to the electropermeabilization effects of the electric fields, promoting the introduction of therapeutic agents into cells within the region.

Although the present invention can be readily applied in any environment in which the delivery of electrical waveforms is considered desirable, the invention is particularly suited for the delivery of electrical waveforms in vivo to patients expected to benefit from such treatment. Such therapeutic uses presently include bone repair, dermal wound healing, nerve regeneration, transport and delivery of therapeutic agents, and the like. For example, the invention will find use in aiding in the administration of therapeutic agents in situations in which such administration has been considered problematic. Among these situations are included chemotherapy, and particularly chemotherapeutic treatment of brain tumors.

As used herein, the term "therapeutic agent" includes pharmacological agents, chemotherapeutic agents, nucleic acids, genes, antibodies and all other compositions which provide therapeutic benefit to a patient in need of treatment. One therapeutic application of electroporation consists of infusion of an anti-cancer drug into the patient, and electroporation of the drug into the tumor cells by applying electric fields between the electrodes.

The present invention provides an array of individual electrodes organized into a geometry which efficiently delivers electrical waveforms to a predetermined region of tissue within a patient. One aspect of this efficiency is to maximize the electrical waveform intensity and uniformity for a given intra-electrode distance while minimizing the actual number of electrodes which must be placed in order to insure complete coverage of the predetermined treatment region In overview, the present invention thus provides an apparatus comprising an electrode array of a pre-determined geometry which can be implanted as a system in situ in a patient. The electrodes are each connected through conductive cables to a high voltage switching device, for example a Cyto Pulse™ PA-101 sequencer (available from Cyto Pulse Sciences, Inc., Columbia, Md.) with software modifications to permit simultaneous activation of multiple electrodes. The switching device will in turn be connected to a suitable power supply or pulse generator, for example, a Cyto Pulse™ PA 2000 or PA 4000 power supply, or a BTX™ T820 power supply (available from Genetronics, San Diego, Calif.). Also provided will be a means for individually addressing the electrodes so that electric fields can be propagated between preselected electrodes in a pattern which insures thorough coverage of the predetermined tissue region. The switching of electrical signals between the individual electrodes can be accomplished by numerous means, e.g. manually, mechanically, electrically, or by means of a circuit controlled by a programmed digital computer. However, the precise mechanism used in switching the electrical signals between individual electrodes will largely be chosen as a matter of convenience. Thus, in certain embodiments, one can separately control each individual electrode, in order to achieve the desired therapeutic effect while minimizing attendant tissue trauma, as disclosed in U.S. patent application Ser. No. 08/476,714, the entire contents of which is incorporated herein by this reference.

As noted previously, the amplitude of the waveform applied to the array is based on the intra-electrode distance and should be selected so as to propagate electric field strengths sufficient to obtain the intended therapeutic benefits. Once the intra-electrode distance is determined and the settings for the power supply are selected, the present array will allow for the efficient delivery of the electrical waveforms to the predetermined tissue region within the patient.

In operation, an array as described above is disposed within the tissue of a host patient so as to adequately define the intended region for therapeutic treatment. Once the array is established and connected to the pulse generator, electric signals are directed to the electrodes in order to propagate electric fields of predetermined amplitude and duration through the tissue between the electrodes. The parameters of the signal are generally selected so that the tissue between the electrodes is subjected to electric fields strengths of high intensity and short duration. The voltage will be adjusted so that the generated field has the desired intensity. These fields will make the membranes of preselected cells in the tissue transiently permeable in order to permit the therapeutic agents to enter the cells in the predetermined region. This transient increase in permeability is believed to result from the temporary formation of pores within the cell membranes large enough to permit migration of the agent through the membrane and into the cytosol.

Figure 16:
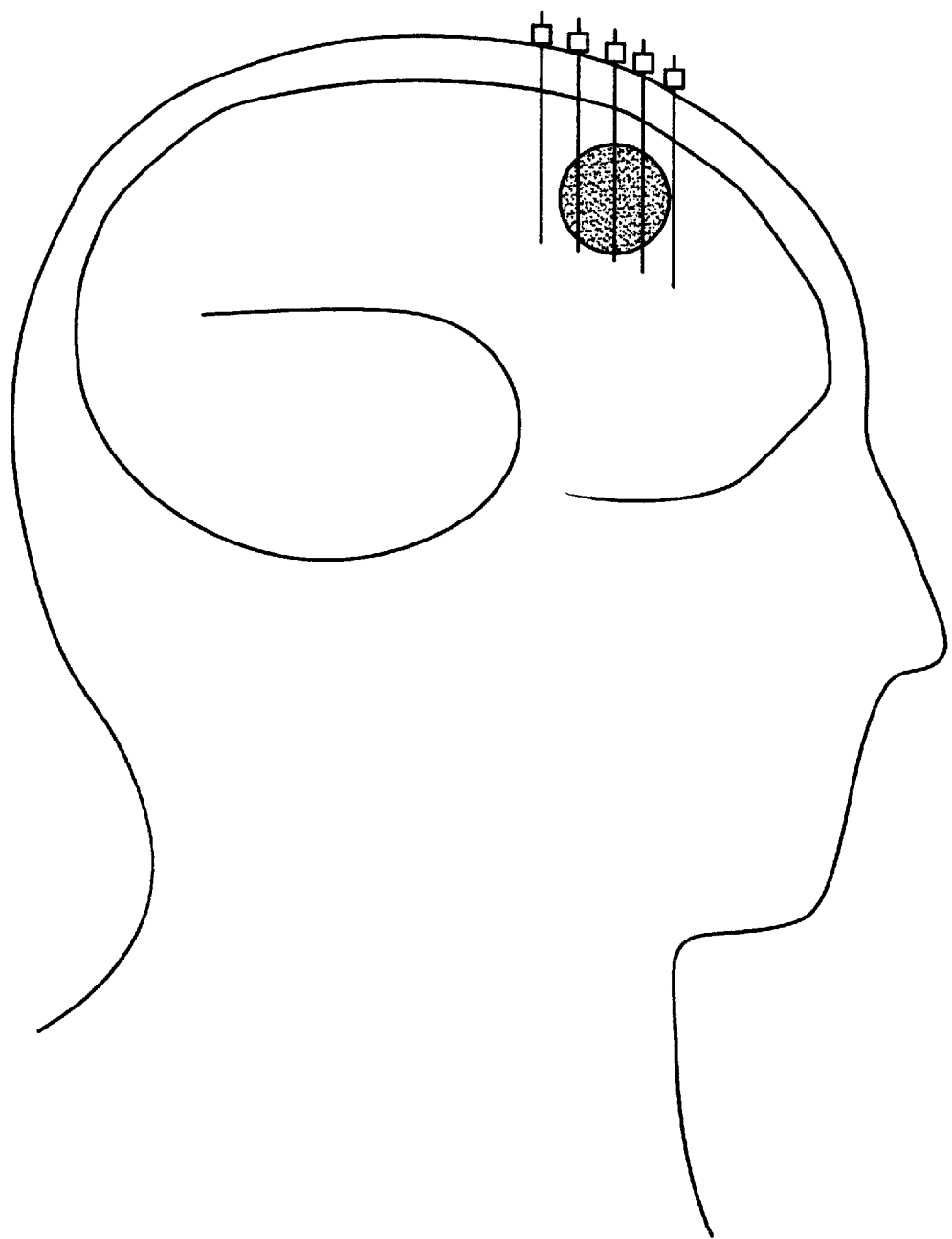
FIG. 16 depicts the placement of an electrode array of the invention in situ in the brain of a patient.

As illustrated in FIG. 4, the present array can be desirably established as conductive rod electrodes 34a, 34b, 34c, optionally mounted on an insulated or dielectric carrier or support member 45 and held in a predetermined geometry while allowing the electrodes to be inserted to a desired depth in the tissue. Alternatively, the electrodes can be implanted individually, and then optionally affixed to a support or directly to the patient (as depicted schematically in FIG. 16). Desirably, the electrodes can be provided with a penetration stop so that the predetermined depth of insertion can be achieved in minimal time. Optionally, the geometry of the array established on the carrier can be subject to adjustment for intra-electrode distance, and a distance spacing sensor may be used to generate a signal either to the operator or directly to the pulse generator so that voltage adjustments can be made in order to establish the desired electric field.

In operation, an array as above described is selected and optionally mounted on a suitable carrier which can then be stereotaxically positioned in relationship to the patient so as to facilitate the accurate and rapid establishment of the electrode array in situ in the patient. In certain embodiments of the invention, acute placement of the electrodes will be made into the peripheral regions of the cavity remaining after surgical resection of a tumor mass. Electrode array geometry can be maintained by a support, while electrode placement and depth would be determined by the surgeon. The therapeutic agent will then be infused into the patient either systemically or by direct injection into the vasculature of the predetermined tissue region or directly into the tissue itself, or by methods as described in application Ser. No. 08/476,714.

The function of the pulse or signal generator is to generate a predetermined electrical waveform which, when applied to the electrodes, results in the propagation of electric fields of the predetermined amplitude and duration through the tissue that is positioned between the electrodes. Preferably, these waveforms are applied repeatedly so as to optimize the electropermeability effect.

In the practice of the invention, two elements are ordinarily controlled to provide the intended benefits: i) the electrical waveform parameters delivered by the signal generator, and ii) the electrical state of each individual electrode within the array during the delivery of the waveform.

Figure 18:
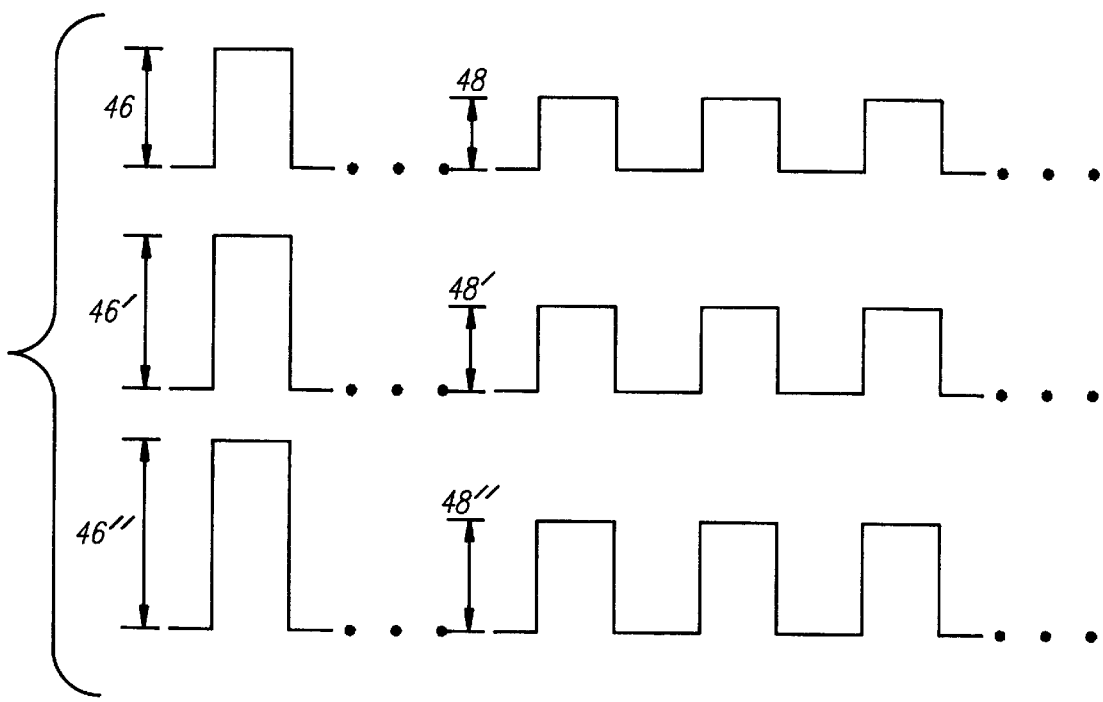
FIG. 18 depicts the cascaded pulses of FIG. 17, followed by pulses creating electric fields of decreasing intensity.

The electrical waveform parameters which can be controlled include the type of waveform, the signal amplitude, and the pulse duration. These individual parameters determine the characteristics of a single pulse. In certain embodiments it is desirable to vary these characteristics between pulses. Pulse-to-pulse variability dictates that one or more individual parameters, such as amplitude, be manipulated from one pulse to the next in order to increase safety or therapeutic efficacy. For example, FIG. 18 depicts a pulse train wherein a high amplitude pulse 46 is followed by a series of lower amplitude pulses 48. Pulse sequences determine the manner in which individual pulses are integrated. In this regard, the number of, and time interval between, individual pulses in a sequence is regulated, as well as the number of pulse sequences in a course of therapeutic treatment (e.g. 46, 46', 46" in FIG. 18).

Figure 11:
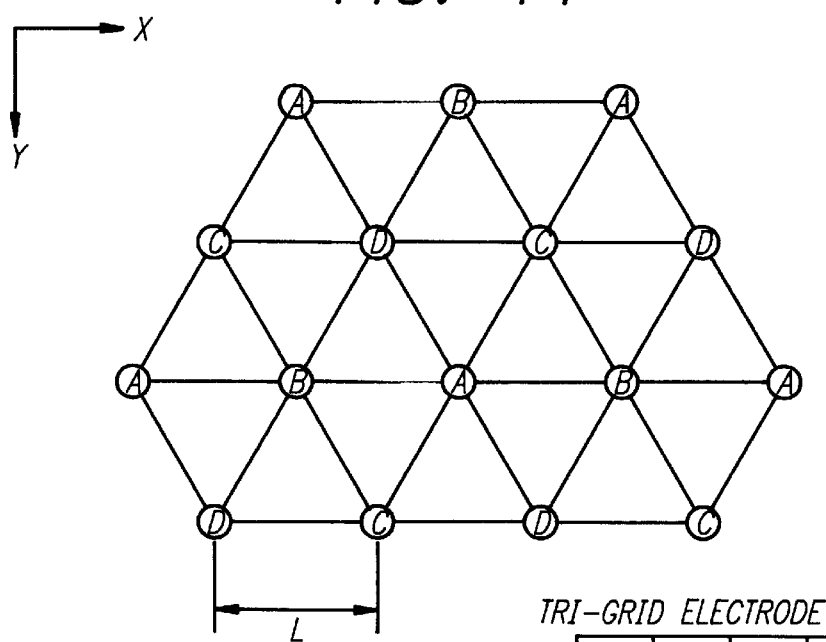
FIG. 11 depicts the use of a four channel control means to activate the tricells in a trigrid, so as to provide the interlocking trilobe field patterns of FIG. 6.

Control of the electrical state of the individual electrodes involves a system capable of individually addressing electrodes within an array. One embodiment of such control would incorporate a high voltage switching device wherein the electrical state of each electrode is controlled by an individual switch. Each switch would have three settings: i) pulse positive (+), ii) pulse negative (−), and iii) open (i.e. off). Together these switches could be electrically activated in any of numerous possible combinations. Although an array of "tricells" can be pulsed in a "trigrid" pattern with only four channels (as depicted in FIG. 11), system flexibility in establishing alternative array patterns suggests the use of individual switches for each electrode in the array.

Where desirable, the integrated control of these and other elements of the invention can be accomplished by utilizing microprocessor or digital computer technologies. Additionally, data pertaining to realtime waveform delivery can be digitized and acquired for evaluation and verification of proper system function. Desirably, such data could be stored within the local system until uploaded to a central computer for further use.

Electric fields will be established within the target tissue by delivery of electrical waveforms to preselected electrodes. The parameters of the signal will define the electric field strength E (in kV/cm) within the tissue. Each protocol and tissue will have its own characteristics which determine the critical field strength for optimum therapeutic effect. This tissue variation is due to cell size, membrane composition and the individual characteristics of the cell membrane itself. Generally, the required field strength varies inversely with the size of the cells contained within the tissue. Mammalian tissue generally requires field strengths of between approximately 0.2 kV/cm to 3 kV/cm for electroporation.

The electrical waveform provided by the generator can be an exponentially decaying pulse, a square pulse, a unipolar oscillating pulse train or a bipolar oscillating pulse train. Square pulses are generally sufficient to implement the majority of techniques. The electric field strength can desirably be between 0.2 kV/cm to 20 kV/cm, more commonly 0.5 kV/cm to 3 kV/cm. The pulse duration can be from 100 nanoseconds to 100 milliseconds and there can be from 1 to 10,000 pulses per second. Of course, the waveform, strength and pulse duration will be dependent on the tissue in the predetermined region and the type of therapeutic agent that is to permeate the cells via electroporation.

In certain embodiments, the present invention provides an apparatus and system for the transport and delivery of therapeutic agents in vivo to a predetermined region of tissue within the host. Such transport and delivery consists of, in part: i) the localized circulatory extravasation of systemically administered therapeutic agents; (ii) the local extracellular infusion of therapeutic agents; (iii) the distribution and concentration of therapeutic agent within the predetermined region of tissue; (iv) the electroporation of cell membranes within the predetermined region of tissue; and (v) the transport of the therapeutic agents into the cytosol of the electroporated cells within the predetermined region of tissue.

Figure 2:
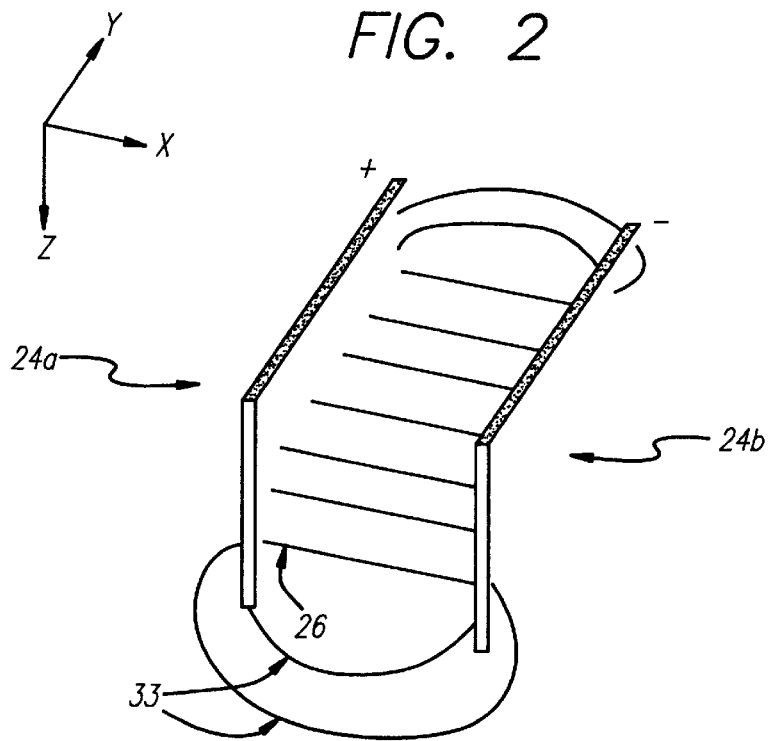
FIG. 2 is a schematic view depicting the field lines and approximate electric field strength for a plate electrode model, wherein the plates generate approximately uniform fields in the central region and weaker fringe electric fields at the edges.
Figure 3:
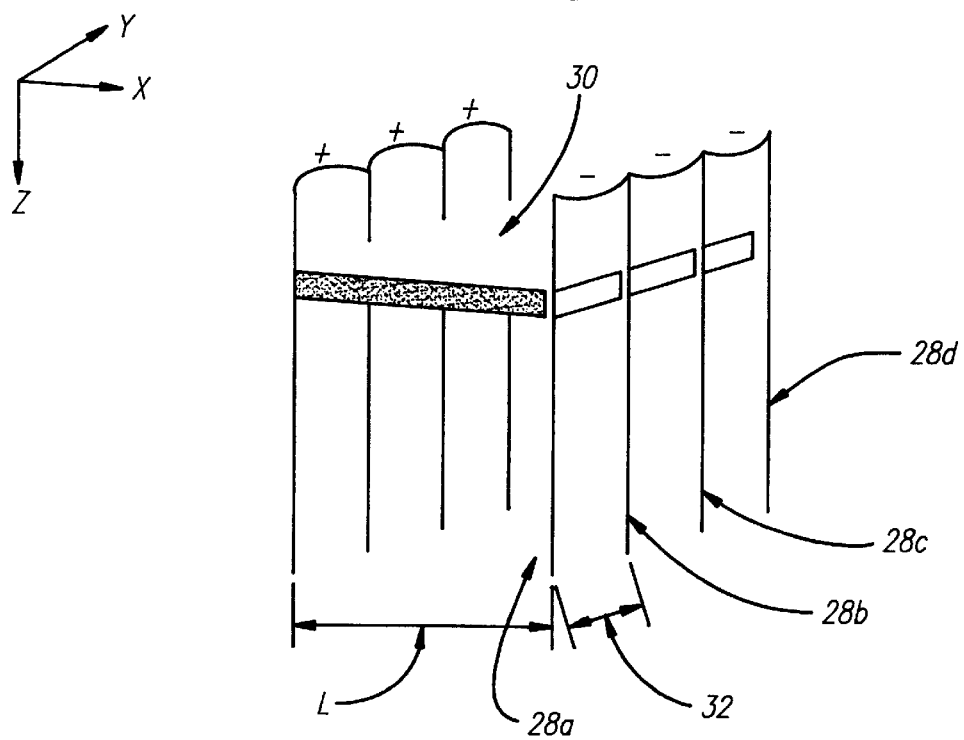
FIG. 3 depicts an electrode array of the prior art which includes spaced apart parallel arrays of needle electrodes mounted on a dielectric support member.

As discussed above, one embodiment of the electrode array, representing a single electrode cell (a tricell as depicted in FIG. 4), is comprised of three individually addressable penetrating electrodes ordinarily of approximately uniform predetermined lengths, desirably of biologically compatible construction and with electrically nonconductive proximal regions and electrically conductive distal regions; such electrically conductive distal regions defining the effective electrode length. In certain embodiments, the effective electrode length of each individual electrode may be different and will be of a predetermined value in order to confine the electric field effects to the predetermined region for tissue treatment. Such predetermination of electrode length shall be of sufficient value as to assure appropriate consideration for the weakened electric field effects encountered at either end of the electrode, as depicted in FIG. 2 (i.e. the field-fringe effect 33).

Figure 5:
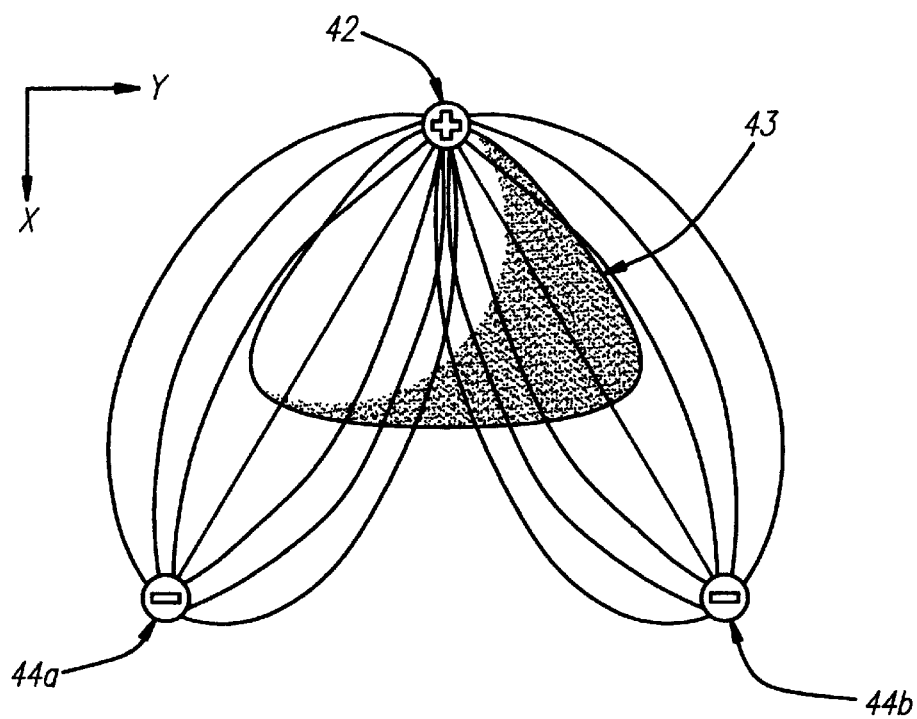
FIG. 5 depicts the electric field generated in the array of FIG. 4 in a characteristic trilobe pattern, wherein the shaded area indicates the region where the electric field strength exceeds the electroporation threshold.
Figure 6:
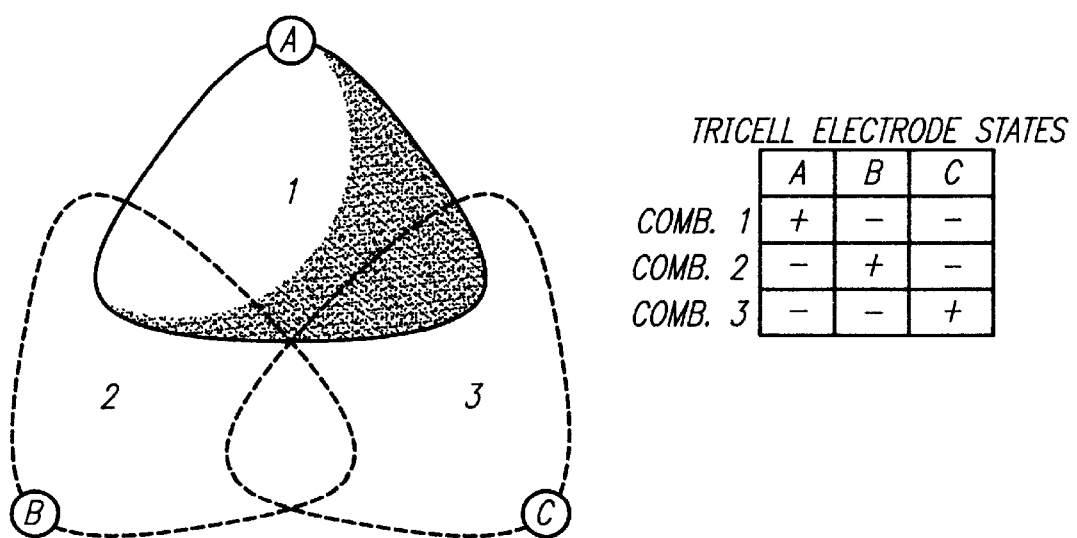
FIG. 6 depicts three interlocking trilobe field patterns resulting from the sequentially shifting electric field activation of the array of FIG. 4.
Figure 7:
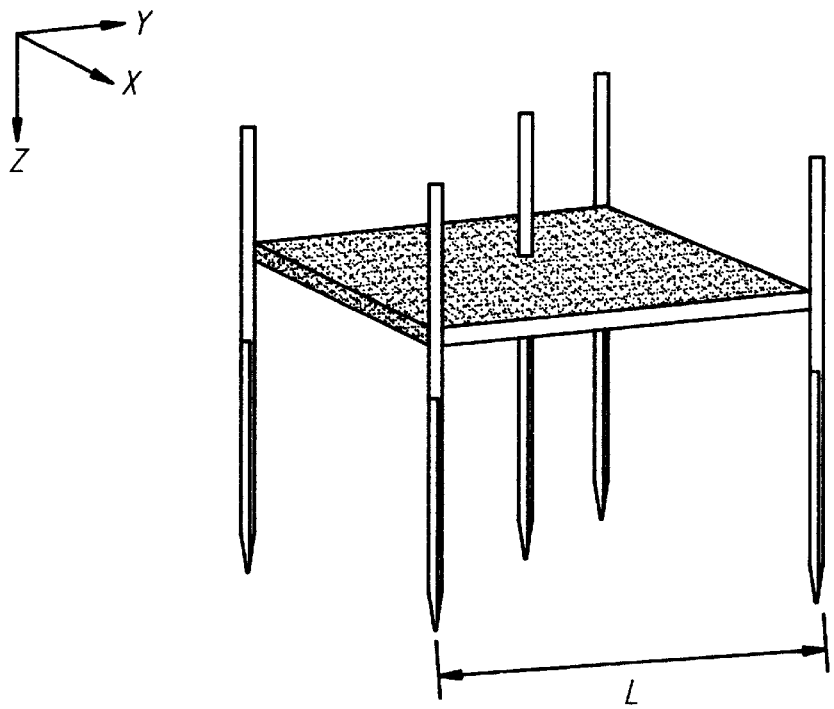
FIG. 7 illustrates a box array of needle electrodes with a core electrode mounted on a dielectric support member.
Figure 8:
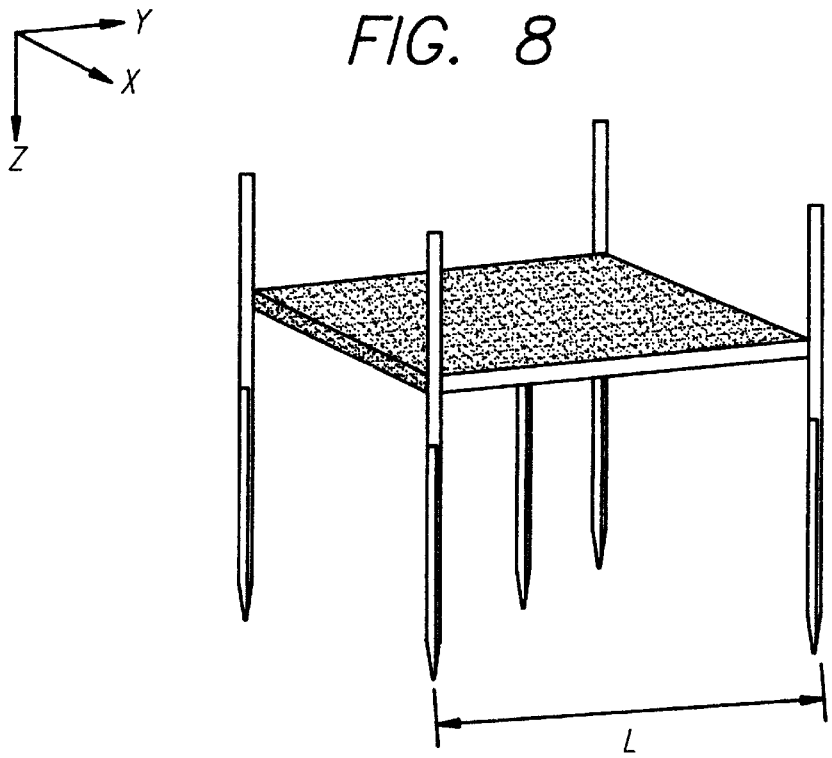
FIG. 8 illustrates a box array of needle electrodes without a core electrode mounted on a dielectric support member.
Figure 9:
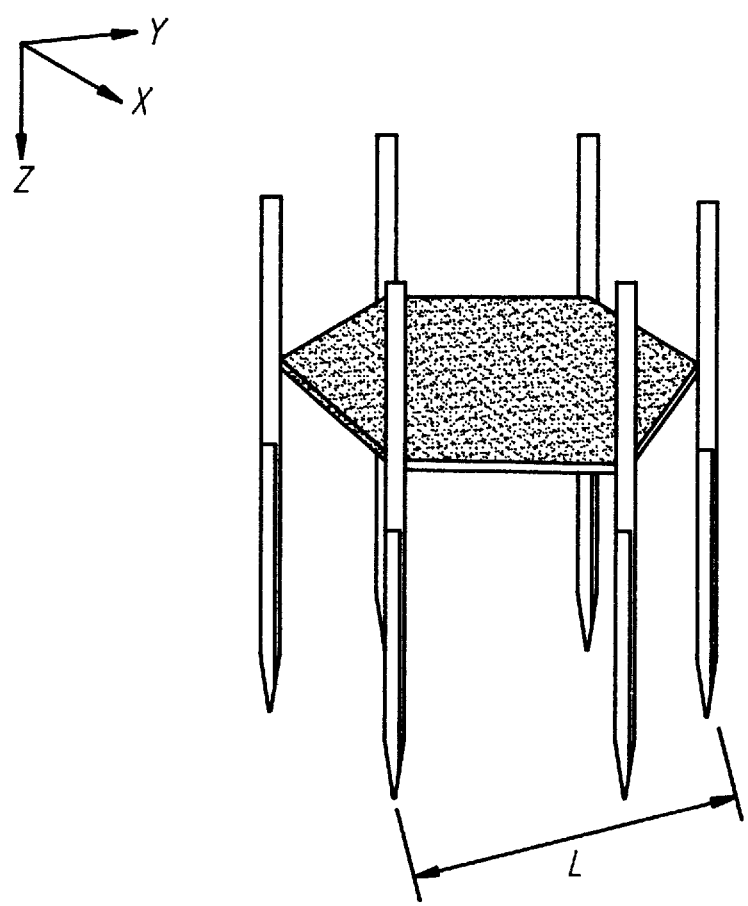
FIG. 9 depicts a hexagonal electrode array of needle electrodes mounted on a dielectric support member.

Of particular benefit, in embodiments dependent on electric field threshold to achieve desired therapeutic effect, such as electroporation, is the manner in which the waveforms are applied to a trigonous portion of the predetermined treatment region through the tricell (see FIG. 5). When applying an electrical waveform by configuring one primary 42 and two secondary electrodes 44a, 44b in each tricell (where the polarity of the primary electrode can be either + or −), the electric field lines converge 43, resulting in relatively uniform, threshold-level field intensities throughout the trigonous region or "trilobe" adjacent to the primary electrode. In a similar manner, the other two electrode configurations can be sequentially pulsed, resulting in three interlaced "trilobes" yielding complete therapeutic coverage of the tricell (see FIG. 6). Selected alternative electrode array geometries are depicted in FIGS. 7, 8 and 9, each having distinct disadvantages when compared to the tricell.

Figure 1B:
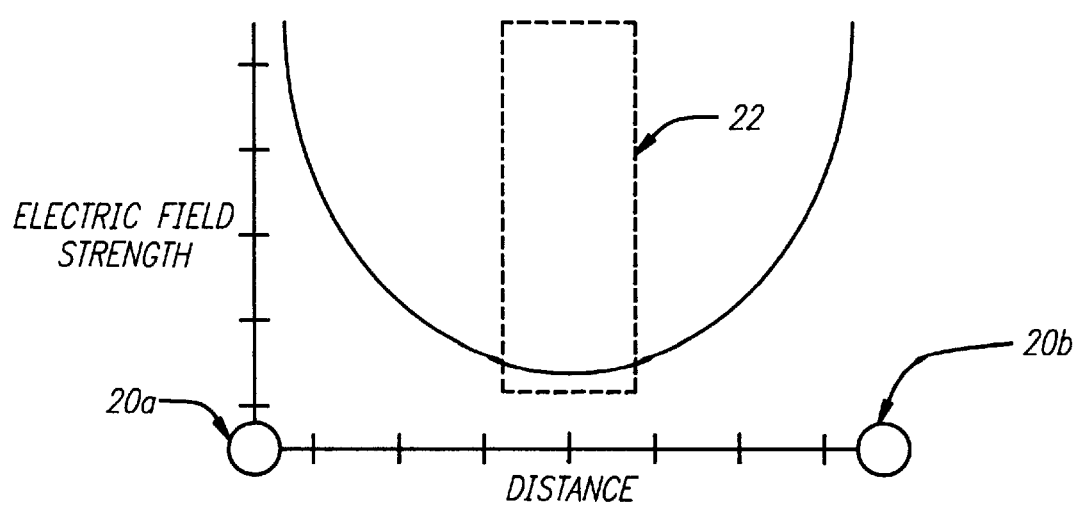

In one embodiment, wherein an electroporation protocol is administered, the voltage applied to electrode pairs is reported in the literature as a function of the distance, "L", between those pairs, typically in kV/cm (see FIGS. 4, 7, 8 and 9). Based upon the literature pertaining to tissue electroporation, it appears that higher voltage commensurate with larger L is more problematic than smaller voltage and the corresponding smaller L, suggesting that one practicing in vivo electroporation cannot simply expand L to any desired distance and expect an overall satisfactory therapeutic effect. Cell lysis due to high electric field strengths around the electrode tract must be considered, as well as the weakened state of the electric field midway between electrode pairs (see FIG. 1); a weakening that is more prevalent in electrode array geometries other than the present tricell array.

Figure 10:
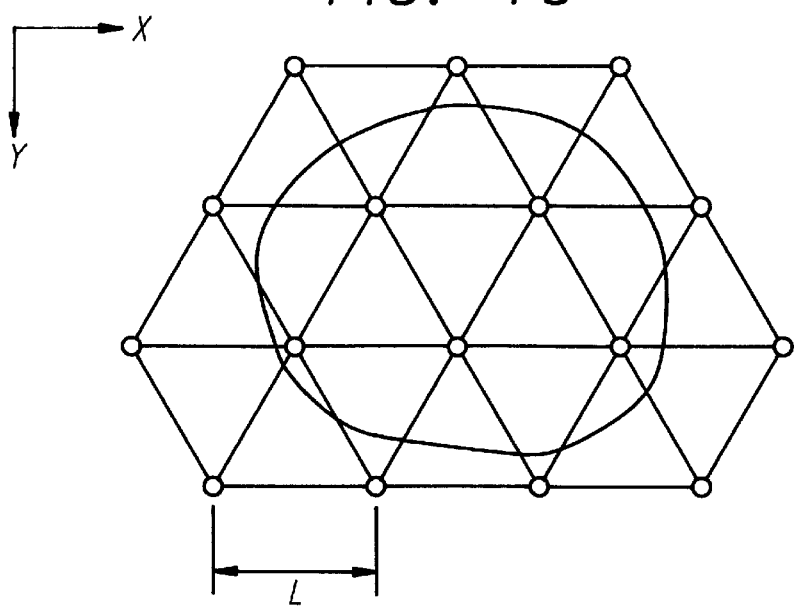
FIG. 10 depicts the expansion of the tricell array of FIG. 4 into a trigrid pattern of interlocking tricells.
Figure 13:
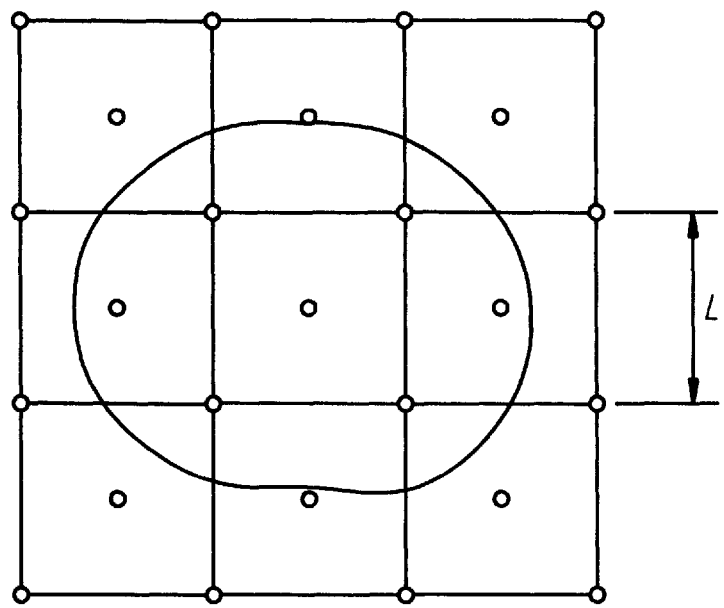
FIG. 13 depicts the expansion of the box array of FIG. 7 into a multi cell grid pattern of overlapping cells.
Figure 14:
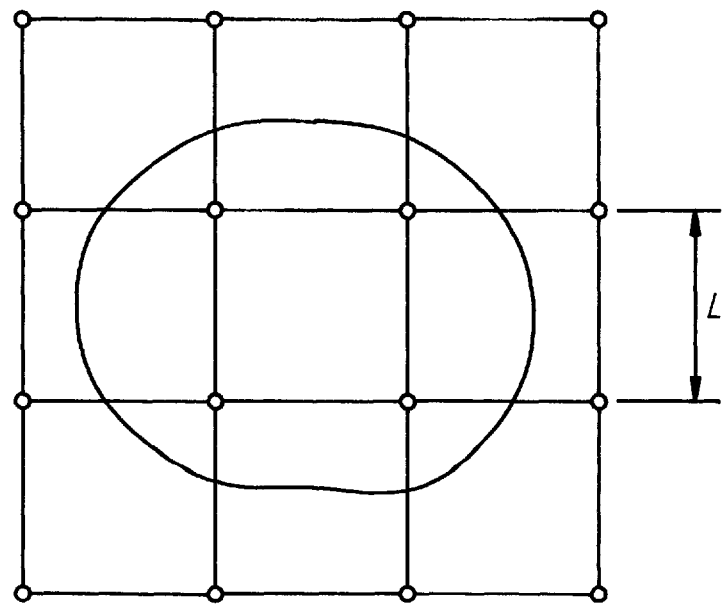
FIG. 14 depicts the expansion of the box array of FIG. 8 into a multi cell grid pattern of overlapping cells.
Figure 15:
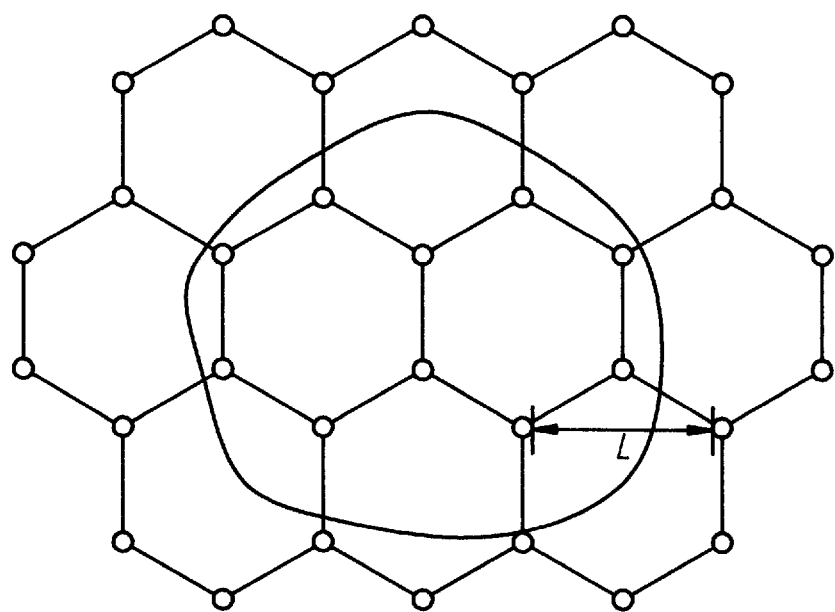
FIG. 15 depicts the expansion of the hexagonal array of FIG. 9 into a multi cell grid pattern of overlapping cells.

Additionally, an optimal efficiency of electrodes used per tissue volume treated must be achieved in order to minimize surgical complications correlated to the number of electrodes implanted and the requisite time spent occupying the operating room. Thus, the present invention also provides an efficient means of expanding the electrode array tricell, or any alternative cell design, into a multi-cell grid for controlled electric field propagation in an expanded cross sectional area of the predetermined region. In order to alleviate many of these potential treatment complications, a tricell as depicted in FIG. 4 can be expanded in a multi-cell pattern (i.e., a "trigrid") to provide therapeutic coverage of the "X" and "Y" dimension of a predetermined treatment region which exceeds the linear dimension L (see FIG. 10). When compared to other electrode designs configured with the same L (see FIGS. 13, 14 and 15), the trigrid offers considerable advantages in uniformity of electric field coverage and efficiency when directly comparing the number of electrodes required to treat a given predetermined treatment region. This advantage is an important consideration in any clinical/surgical application. One benefit of this expansion into a trigrid is that once the basic tricell is established, each additional electrode placed in the array creates at least one and possibly two additional cells in the array grid.

Figure 12:
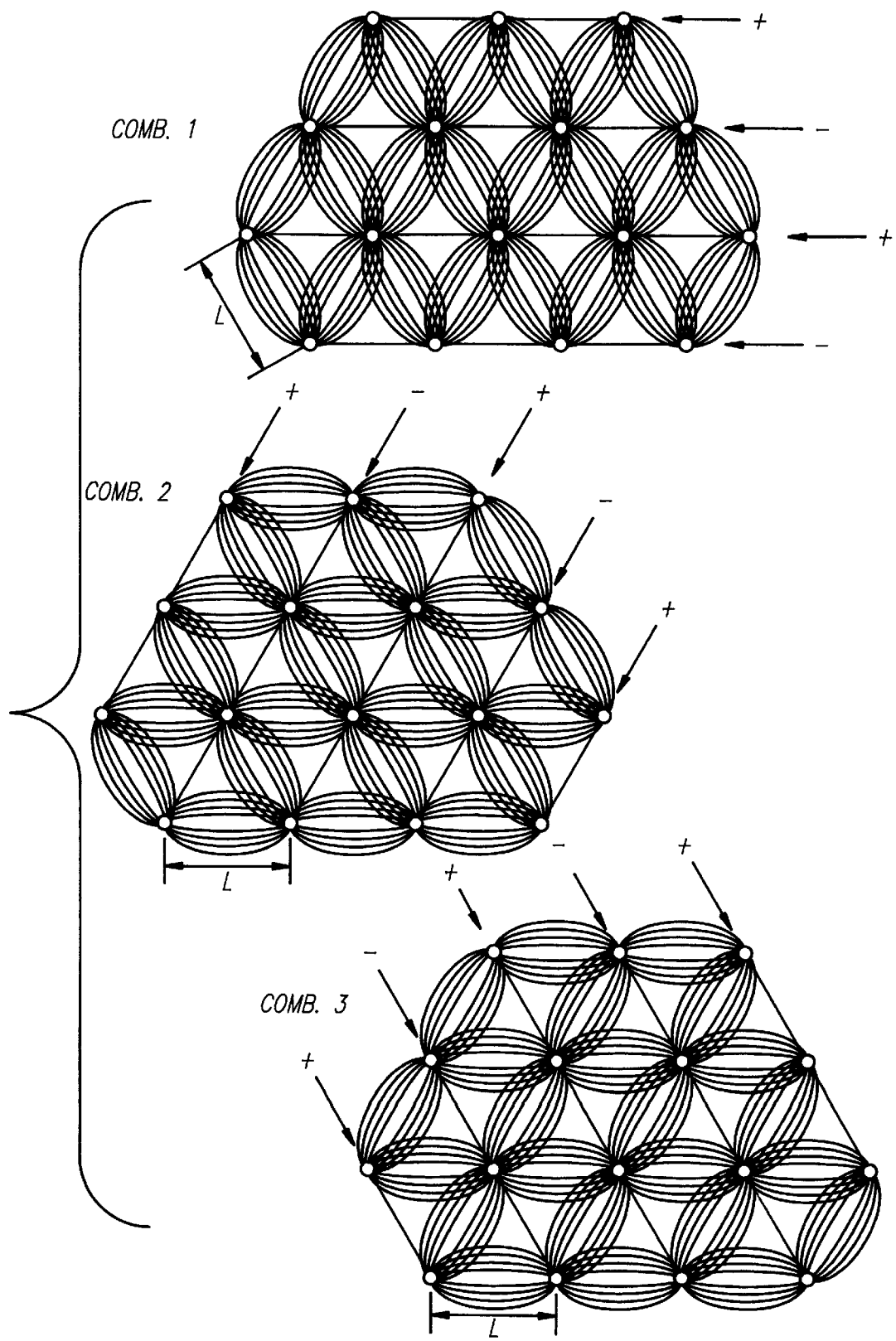

Of further benefit in certain embodiments is the manner in which the trigrid can be pulsed in a tricell-interlocking manner, as depicted in FIG. 12. This pattern provides complete therapeutic coverage of the predetermined treatment region with only three pulse combinations (see FIG. 6), and requires only four electrode channels (see FIG. 11) regardless of the number of electrodes in the complete array. Overall tissue trauma during surgery is thus minimized, a unique characteristic of the trigrid array.

Utilizing information provided by MRI, CT scan, or other methods, the optimal trigrid pattern and effective electrode length can be determined, thus defining the predetermined region targeted for treatment. In either tricell or trigrid fashion, these electrodes may be placed acutely for single treatment or chronically for a series of treatments to the same predetermined region in the patient.

Figure 17:
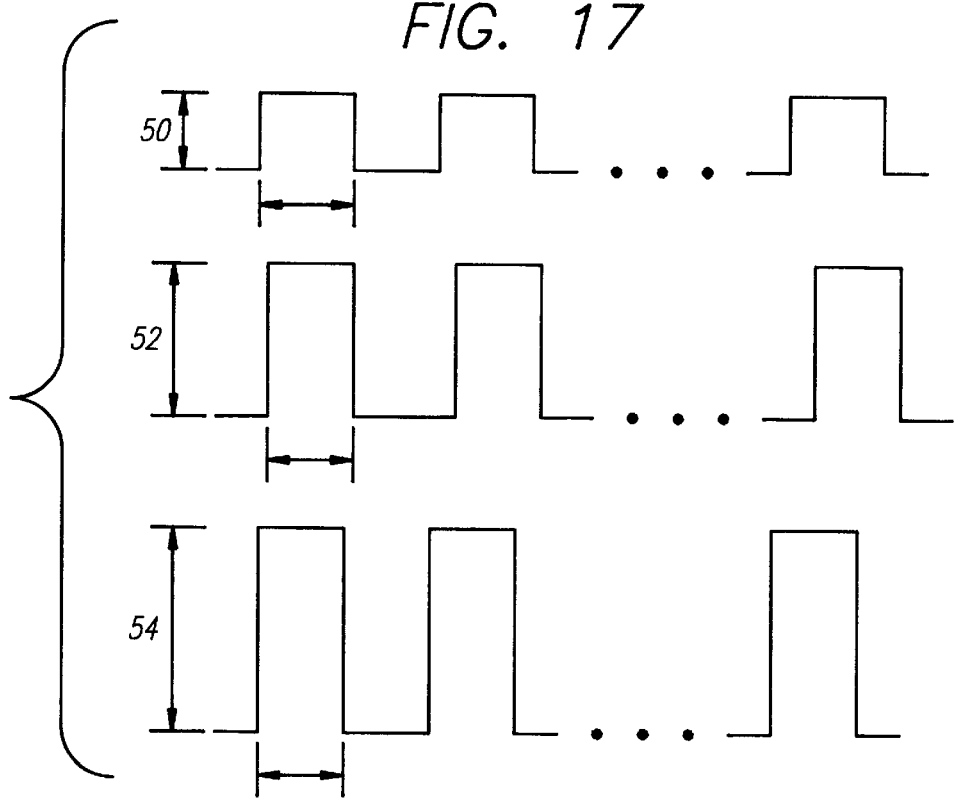
FIG. 17 depicts cascaded electrical signal pulses of increasing electric field intensity.

To mitigate cell lysis associated with the more intense electric fields around the electrodes (inherent to some embodiments), a localized hyperconductance of the extracellular fluids may be desirable in order to partially shunt or shift field intensities away from the electrode milieu and toward the more central portions of L in the predetermined region. This may be accomplished by direct injection of hyperconductive solutions by local injection, or by infusion through a hollow core in the electrode. Alternatively, in certain embodiments, such as electroporation, electrical pulse parameters determined to be of therapeutic benefit may be adapted in such a way as to initially induce localized increases in the conductance of the electrode milieu. One method of inducing such effect is a cascaded pulse sequence (see FIG. 17) where applied voltages are cascaded from lower values initially 50, being progressively increased in each subsequent round 52, 54, and reaching optimal therapeutic pulse parameters in a final round of pulsing.

In embodiments involving Iontophoresis, electrically charged therapeutic agents are desirably distributed through and concentrated within the predetermined region by means of electrical waveforms delivered through the individually addressable electrodes of the present invention.

During electroporation, the transmembrane delivery of therapeutic agent into the cytosol of the permeabilized cells is commonly believed to occur by diffusion. Electroosmosis may enhance this transmembrane delivery. In one embodiment, electrical waveforms of a lesser intensity (48, 48', 48" in FIG. 18) are delivered through the individually addressable electrodes of the present invention, after the electroporation waveforms have been delivered and before cell membrane resealing, in order to enhance the transport of the extracellular therapeutic agents into the cytosol of the electroporated cells.

The following examples serve to illustrate certain preferred embodiments and aspects of the present invention and are not to be construed as limiting the scope thereof.

EXPERIMENTAL

In the experimental disclosure which follows, all weights are given in grams (g), milligrams (mg), micrograms (μg), nanograms (ng), or picograms (pg), all amounts are given in moles (mol), millimoles (mmol), micromoles (μmol), nanomoles (nmol), picomoles (pmol), or femtomoles (fmol), all concentrations are given as percent by volume (%), proportion by volume (v:v), molar (M), millimolar (mM), micromolar (μM), nanomolar (nM), picomolar (pM), femtomolar (fM), or normal (N), all liquid volumes are given in liters (L), milliliters (mL), or microliters (μL), all solid volumes are given in cubic centimeters (cc), and linear measurements are given in millimeters (mm), micrometers (μm), or nanometers (nm), unless otherwise indicated.

The following examples demonstrate the practice of the present invention in delivering electrical waveforms to tumor tissue.

EXAMPLE 1

Tumor Model Used in Survival Studies

The experimental brain tumor model employed in the following examples was the 9L gliosarcoma in the female Fischer rat. Tumor implants consisted of 200,000 9L gliosarcoma cells suspended in 2.3 μL of Dulbecco's Phosphate Buffered Saline with 2% rat serum. After anesthetization by intra peritoneal injection of a ketamine/xylazine mixture, the scalp was shaved and swabbed with Betadine® solution. After placement in a stereotaxic apparatus, a 1 cm incision was made in the scalp above bregma. A burr hole was drilled in the skull 1 mm anterior and 3 mm lateral of bregma. The injection needle was lowered stereotactically 4 mm deep, into the right caudate nucleus. After slow injection of the cells (4 minutes for 2.3 μL), the needle was raised and the burr hole was sealed with bone wax. After careful irrigation of the area, the wound was closed with surgical staples.

EXAMPLE 2

Single Treatment—Triangle Electrode Array (Tricell).

On the eighth day post implantation (tumor mass approximately 0.02 cc), the rats were again anesthetized with an i.p. injection of a ketamine/xylazine mixture. After placement in the stereotaxic apparatus, the scalp was again disinfected with Betadine®. Another incision was made in the scalp and the burr hole was located. An electrode array comprising three elongate rod electrodes oriented in an approximate equilateral triangle was then placed in the stereotactic arm. The array was then placed around the burr hole so that each electrode was approximately equidistant from the implant hole. New burr holes were drilled to accommodate the electrodes. The array was then lowered with the stereotaxic arm to a depth of 5 mm.

The femoral vein of the animal was then exposed and 1 unit of bleomycin per kg of bodyweight was injected intravenously over approximately fifteen seconds. After 30 minutes to allow circulation of the bleomycin, the animals were exposed to a regimen of brief high voltage pulses. Each pulse had an amplitude of 450 volts (1 kV/cm based on the established electrode spacing) and a duration of 100 μs. Four pulses were applied at each of three single-primary-two secondary electrode combinations (see FIG. 5). After completion of the pulse regimen, the animals were injected intravenously with a 0.5 mg/kg dose of the steroid dexamethasone. Finally, the electrode array was slowly extracted, the burr holes sealed with bone wax, and the incision sealed with surgical staples.

Figure 19:
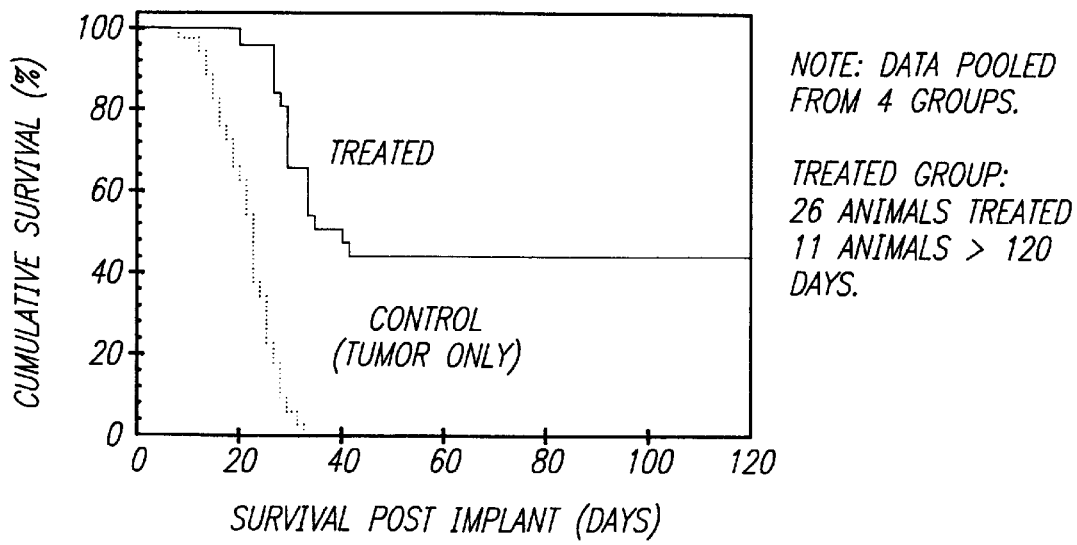
FIG. 19 is a Kaplan-Meier survival chart for the experimental subjects described in example 2.

Results: In FIG. 19, a Kaplan-Meier survival chart illustrates the survival rates for 26 animals treated as described. The x-axis represents days of survival and the y-axis represents the percentage of subject alive on the selected day. As FIG. 19 demonstrates, 120 days after implant 43% of the treated animals survived, and showed no outward signs of the presence of a tumor mass. The dashed line represents a control group which received no treatment.

After 120 days, five of the 11 surviving subjects were sacraficed by cardiac perfusion with 150 mL of formalin. The brains of three subjects were then sectioned horizontally at 1 mm, 2 mm, and 4 mm with a thickness of 5 μm. The tissue sections were stained with hematoxylin and eosin. Pathological examination revealed that no viable tumor cells remained in any of the tissue sections.

EXAMPLE 3

Multiple Treatments—Triangle Electrode Array (Tricell)

Several survival studies have been performed to determine the benefit of multiple treatments. The tumor model from Example 1 was again employed for these experiments. Animal subjects were treated on day eight post-implantation with the protocol outlined in Example 2 for the triangle electrode arrays. On day eleven, the animals were re-anesthetized and, after reopening the scalp and removing the bone wax plugs, the electrodes were lowered into the existing burr holes. The identical treatment procedure was then performed on the animal.

Figure 20:
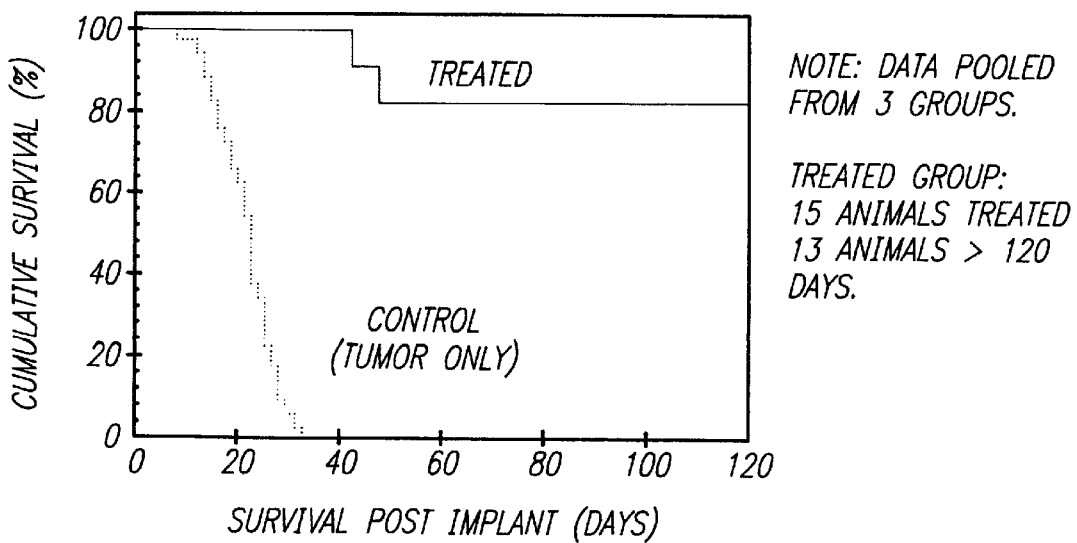
FIG. 20 is a Kaplan-Meier survival chart for the experimental subjects described in example 3.

Results: In FIG. 20, a Kaplan-Meier survival chart illustrates the survival rates for the multiple treatment groups. Fifteen animals received the two treatment procedure as described. As FIG. 20 demonstrates, 120 days after implant 87% of the treated animals survived, and showed no outward signs of the presence of a tumor mass. The dashed line represents a control group which received no treatment.

The brains of six of the 13 surviving subjects were then prepared according to the histological procedure of Example 2. Pathological examination of the tissue sections revealed no residual tumor.

EXAMPLE 4

Multiple Treatments with Multicell Array (Trigrid)

In order to demonstrate the concept of expanding individual cells into a grid format a two-cell triangle (interlocked tricells) was tested on the tumor model from Example 1. Four electrodes were arranged into two approximately equilateral triangles with sides of 3 mm. The preparation procedure from example 3 was followed for each subject. The electrode array was lowered to a depth of 5 mm. The pulsing regimen was based on the trigrid pulsing pattern outlined in FIG. 12.

"Tri-grid" pulsing: Thirty minutes after the injection of the bleomycin agent, the array was pulsed four times in each of three combinations with a magnitude of 300 volts (1 kV/cm based on electrode spacing) and a pulse duration of 100 μsec. The electrodes were pulsed so that each "cell" was configured with a single primary and two secondary electrodes. All four of the electrodes were active in each configuration, creating an interlocking triangle array.

Figure 21:
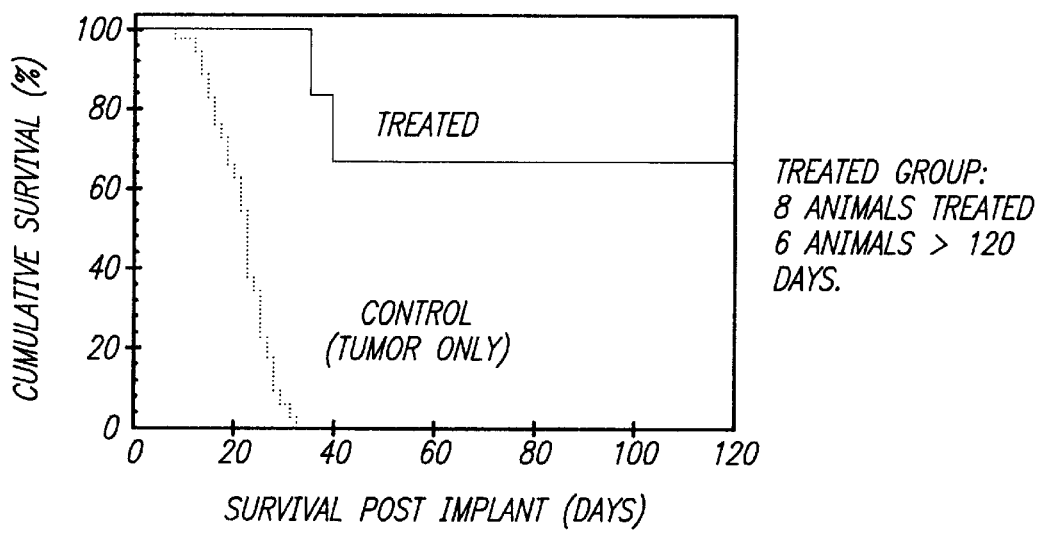
FIG. 21 is a Kaplan-Meier survival chart for the experimental subjects described in example 4.

Results: In FIG. 21, a Kaplan-Meier survival chart illustrates the survival rates for the animals treated as described. As FIG. 21 demonstrates, 120 days after implant 75% of the treated animals survived, and showed no outward signs of the presence of a tumor mass. The dashed line represents a control group which received no treatment.

The brains of the six surviving subjects were then prepared according to the histological procedure of Example 2. Pathological examination of the tissue sections revealed no residual tumor.

EXAMPLE 5

Protocols for Control Subjects

Three control protocols were performed to compare with the treatment groups. All subjects were implanted according to the procedure outlined in Example 1. The first group of 35 rats received no treatment (Drug (D)–, Electrical Pulsing (EP)–). The second group of eight rats were treated on day eight post implant in accordance with the procedure of Example 2, except they did not receive the therapeutic agent (D–, EP+). The third group of eight rats were treated on day eight post implant in accordance with the procedure of Example 2, except they did not receive the electrical pulses (D+, EP–).

Figure 22:
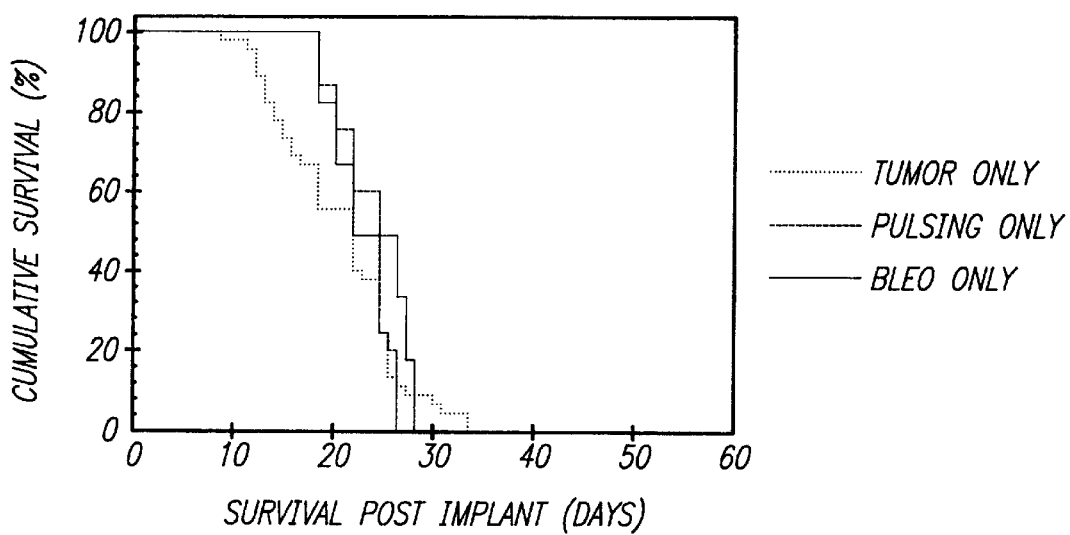
FIG. 22 is a Kaplan-Meier survival chart for the experimental subjects described in example 5.

Results: In FIG. 22, a Kaplan-Meier survival chart illustrates the survival rates for the animals in the control protocols. As FIG. 22 demonstrates, no animals from any of the control protocols survived beyond 32 days after implant. There was no significant difference in survival between any of the groups (D– EP–, D– EP+, D+, EP–), demonstrating that both the therapeutic agent and the electrical pulse regimen are necessary for significant increase in survival.

All patents and patent applications cited in this specification are hereby incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the disclosure that certain changes and modifications may be made thereto without departing from the spirit or scope of the appended claims.

I claim:

1. An apparatus for the delivery of electrical waveforms comprising:
    an electrode array having at least three individually addressable electrodes disposed so as to form a triangle in a plane intersecting said electrodes; and
    electrical signal generating means operatively connected to said individually-addressable electrodes for delivering electrical waveforms to said electrodes and generating electroporation-inducing electrical fields between said electrodes said at least three individually addressable electrodes simultaneously.

2. An apparatus as recited in claim 1 wherein the electrodes are elongate.

3. An apparatus as recited in claim 2 wherein the elongate electrodes are oriented in approximately parallel directions.

4. An apparatus as recited in claim 1 wherein the triangle is of approximately equilateral geometry.

5. An apparatus as recited in claim 1 wherein each of said electrodes comprises an electrically conductive region and an electrically nonconductive region.

6. An apparatus as recited in claim 1 wherein said array comprises at least four electrodes disposed so as to form two interconnected triangles in a plane intersecting said electrodes.

7. A system for the delivery of electrical waveforms to a patient comprising:
    means for implanting in a patient an electrode array having at least three individually addressable electrodes disposed so as to form a triangle in a plane intersecting said electrodes; and
    electrical signal generating means operatively connected to said individually-addressable electrodes for delivering electrical waveforms to said electrodes and generating electroporation-inducing electrical fields between said said at least three individually addressable electrodes simultaneously.

8. A system as recited in claim 7 wherein the electrodes are elongate.

9. A system as recited in claim 8 wherein the elongate electrodes are oriented in approximately parallel directions.

10. A system as recited in claim 7 wherein the triangle is of approximately equilateral geometry.

11. A system as recited in claim 7 wherein each of said electrodes comprises an electrically conductive region and an electrically nonconductive region.

12. A system as recited in claim 11 wherein the electrically conductive region of said electrodes and the geometry of said array define a predetermined treatment area for said patient.

13. A system as recited in claim 7 wherein said array comprises at least four electrodes disposed so as to form two interconnected triangles in a plane intersecting said electrodes.

14. An apparatus for the delivery of electrical waveforms comprising:
    an electrode array having at least four individually addressable electrodes disposed so as to form a plurality or triangles in a plane intersecting said electrodes wherein each such triangle shares a common side with an adjacent triangle; and
    electrical signal generating means operatively connected to said individually-addressable electrodes for delivering electrical waveforms to said electrodes and generating electroporation-inducing electrical fields between said at least three individually addressable electrodes simultaneously.

15. An apparatus for the delivery of electrical waveforms comprising:
    a plurality of elongate individually addressable electrodes each having a proximal end and a distal end and comprising:
        means for connecting the proximal end of each said electrode to a source of electrical signals,
        an electrically conductive region located distal to said connecting means, and
        at least one of said electrodes having an electrically nonconductive region located adjacent to said connecting means; and
    electrical signal generating means operatively connected to said individually-addressable electrodes for delivering electrical waveforms to said electrodes and thereby generating electroporation-inducing electrical fields between said said at least three individually addressable electrodes simultaneously.

16. An apparatus for the delivery of electrical waveforms according to claim 15, wherein the plurality of elongate individually addressable electrodes comprises an electrode array having at least three individually addressable electrodes which are disposed so as to form a triangle in a plane intersecting said electrodes, whereby the disposition of the electrodes and the electrically conductive regions of the electrodes determine a three-dimensional region wherein the electrical waveforms propagate an electric field therebetween.

17. A system for the delivery of electrical waveforms to a patient according to claim 16 further comprising means for implanting said electrode array in a patient so that a three-dimensional region of tissue is established wherein the electrical waveforms propagate an electric field substantially confined to said region.

18. A system for the delivery of electrical waveforms to a patient comprising:

means for implanting in a patient an electrode array having at least three individually addressable electrodes disposed so as to form a triangle in a plane intersecting said electrodes; and electrical signal generating means operatively connected to said individually-addressable electrodes for delivering electrical waveforms to said electrodes and generating electroporation-inducing electrical fields between at least one reference electrode and a plurality of satellite electrodes.

19. A system as recited in claim 18 wherein the electrodes are elongate and are oriented in approximately parallel directions.

20. A system as recited in claim 18 wherein the electrodes are elongate and each of said electrodes comprises an electrically conductive region and an electrically nonconductive region.

21. A system as recited in claim 20 wherein the electrically conductive region of said electrodes and the geometry of said array define a predetermined treatment area for said patient.

* * * * *